(12) United States Patent
Schabbach et al.

(10) Patent No.: US 12,257,422 B2
(45) Date of Patent: Mar. 25, 2025

(54) DEVICE FOR ADMINISTERING A MEDICINAL LIQUID BY INJECTION

(71) Applicant: Sanofi, Paris (FR)

(72) Inventors: Michael Schabbach, Frankfurt am Main (DE); Anna Baccaro, Frankfurt am Main (DE)

(73) Assignee: Sanofi, Paris (FR)

( * ) Notice: Subject to any disclaimer, the term of this patent is extended or adjusted under 35 U.S.C. 154(b) by 256 days.

(21) Appl. No.: 16/973,976

(22) PCT Filed: Jun. 13, 2019

(86) PCT No.: PCT/EP2019/065507
§ 371 (c)(1),
(2) Date: Dec. 10, 2020

(87) PCT Pub. No.: WO2019/238825
PCT Pub. Date: Dec. 19, 2019

(65) Prior Publication Data
US 2021/0244884 A1 Aug. 12, 2021

(30) Foreign Application Priority Data

Jun. 14, 2018 (EP) ..................................... 18305728

(51) Int. Cl.
*A61M 5/24* (2006.01)
*A61M 5/315* (2006.01)
*A61M 5/32* (2006.01)

(52) U.S. Cl.
CPC ........ *A61M 5/2425* (2013.01); *A61M 5/2466* (2013.01); *A61M 5/31591* (2013.01); *A61M 5/3232* (2013.01)

(58) Field of Classification Search
CPC ............ A61M 5/2425; A61M 5/31591; A61M 5/3232; A61M 5/24; A61M 5/3234;
(Continued)

(56) References Cited

U.S. PATENT DOCUMENTS 2,514,575 A * 7/1950 Hein .................... A61M 5/2425
604/202
2,669,230 A 2/1954 Smoot
(Continued)

FOREIGN PATENT DOCUMENTS

JP 2014-532524 12/2014
JP 2015-091453 5/2015
(Continued)

OTHER PUBLICATIONS

PCT International Preliminary Report on Patentability in International Application No. PCT/EP2019/065507, dated Dec. 15, 2020, 7 pages.
(Continued)

*Primary Examiner* — Emily L Schmidt
*Assistant Examiner* — Antarius S Daniel
(74) *Attorney, Agent, or Firm* — Bond, Schoeneck & King, PLLC

(57) ABSTRACT

A device for administering a medicinal liquid by injection is provided. The device comprises a dose assembly comprising collapsible reservoir. The device further includes at least one actuator element onto which the user may apply a force to actuate the device, the force having a component along an axis perpendicular to a longitudinal axis; and a housing comprising a septum. The at least one actuator element is configured and arranged to act on at least a portion of a dose assembly and the at least one actuator element and dose assembly are configured and arranged such that the needle is displaceable along the longitudinal axis and/or in an axis parallel to the longitudinal axis in response to an actuation force so that a portion of the needle moves from an interior to an exterior of the housing and device to allow for dispensation of the medicinal liquid.

20 Claims, 4 Drawing Sheets

(58) Field of Classification Search
CPC ............... A61M 5/322; A61M 5/3287; A61M 5/31525; A61M 5/20; A61M 2005/14252; A61M 2005/1585; A61M 2005/206
See application file for complete search history.

(56) References Cited

U.S. PATENT DOCUMENTS

| | | | | |
|---|---|---|---|---|
| 2,693,186 | A * | 11/1954 | Riker | A61M 5/2033 604/139 |
| 3,892,237 | A * | 7/1975 | Steiner | B67B 7/92 604/157 |
| 6,599,272 | B1 * | 7/2003 | Hjertman | A61M 5/315 604/209 |
| 2005/0151105 | A1 * | 7/2005 | Ryan | A61M 39/26 251/149.6 |
| 2006/0200073 | A1 * | 9/2006 | Radmer | A61M 5/14248 604/93.01 |
| 2010/0179473 | A1 | 7/2010 | Genosar | |
| 2011/0144616 | A1 * | 6/2011 | Michaud | F16J 15/56 604/153 |
| 2011/0306929 | A1 | 12/2011 | Levesque et al. | |
| 2013/0006216 | A1 * | 1/2013 | Taylor | A61M 5/2459 604/173 |
| 2013/0245574 | A1 | 9/2013 | Powers et al. | |
| 2014/0207104 | A1 | 7/2014 | Vouillamoz et al. | |
| 2014/0296782 | A1 * | 10/2014 | Ulrich | A61M 5/31 604/173 |
| 2017/0165452 | A1 * | 6/2017 | Frey | A61M 25/00 |
| 2018/0085527 | A1 | 3/2018 | Taylor et al. | |

FOREIGN PATENT DOCUMENTS

| | | |
|---|---|---|
| JP | 2015-533603 | 11/2015 |
| JP | 2017-520344 | 7/2017 |
| WO | WO 2011/094025 | 8/2011 |
| WO | WO 2013/070715 | 5/2013 |
| WO | WO 2014/096957 | 6/2014 |
| WO | WO 2016/007438 | 1/2016 |

OTHER PUBLICATIONS

PCT International Search Report and Written Opinion in International Application No. PCT/EP2019/065507, dated Jul. 10, 2019, 10 pages.

* cited by examiner

DEVICE FOR ADMINISTERING A MEDICINAL LIQUID BY INJECTION

CROSS REFERENCE TO RELATED APPLICATIONS

The present application is the national stage entry of International Patent Application No. PCT/EP2019/065507, filed on Jun. 13, 2019, and claims priority to Application No. EP 18305728.0, filed on Jun. 14, 2018, the disclosures of which are incorporated herein by reference.

TECHNICAL FIELD

The present disclosure relates to a device for administering a medicinal liquid by injection, in particular a single dose of a medicinal liquid.

BACKGROUND

Many medicaments have to be injected into the body. This applies in particular to medicaments, which are deactivated or have their efficiency remarkably decreased by oral administration, e.g. proteins (such as insulin, growth hormones, interferons), carbohydrates (e.g. heparin), antibodies and the majority of vaccines. Such medicaments are predominantly injected by means of syringes, medicament pens or medicament pumps.

The user of such syringes, medicament pens or medicament pumps can range from healthcare professionals to the medicament-recipient themselves, the latter ranging from children or elderly persons. The medicinal injections may include repetitive or multiple injections of a particular dose (e.g. a vaccine in multi-dosage regimen) to a single injection of a single dose (e.g. a vaccine or in an emergency hydrocortisone).

SUMMARY

It would be desirable to provide a device for administering a medical liquid by injection that would conveniently allow the delivery of a single dose, which at the same time are potentially easy to use for the range of potential users including users with limited strength.

According to one aspect, there is provided a device for administering a medicinal liquid by injection, the device comprising
  a dose assembly comprising
    a collapsible reservoir, wherein the collapsible reservoir is adapted to hold the medicinal liquid to be administered;
    an injection needle, wherein at least a major part of the needle defines an longitudinal axis and wherein prior to injection the needle is located in the interior of the device; and
  at least one actuator element onto which the user may apply a force to actuate the device, said force having a component along an axis perpendicular to the longitudinal axis;
wherein the at least one actuator element is configured and arranged to act on at least a portion of the dose assembly and wherein the at least one actuator element and dose assembly are configured and arranged such that the needle is displaceable along said longitudinal axis and/or in an axis parallel to said longitudinal axis in response to an actuation force so that a portion of the needle moves from the interior to the exterior of the device to allow for dispensation of the medicinal liquid.

To further facilitate ease in use as well as safety and potentially disposability, it is desirable that the at least one actuator element and dose assembly are configured and arranged, such that after dispensation of the medicinal liquid and/or release of said at least one actuator element by the user, said portion of the needle moves from the exterior to the interior of the device.

Desirably the collapsible reservoir contains a single dose of medicinal liquid to be administered, in particular a dose having a volume of 1000 µl or less.

Favorably at least a major portion of the walls of the collapsible reservoir of the reservoir is made of a flexible material, in particular such that when the collapsible reservoir contains the medicinal liquid to be administered, the at least major portion of the walls of the reservoir is in an extended or expanded state, and when the medicinal liquid has been dispensed (or when the collapsible reservoir is empty), the at least major portion of the walls of the reservoir is in a collapsed state.

The collapsible reservoir may be desirably configured as a flexible pouch or ampoule. For example the collapsible reservoir may be configured as a flexible ampoule (e.g. having a balloon-like form), where essentially all the walls defining the interior chamber of the reservoir when the reservoir is in an extended or expanded state are made of a flexible material. Alternatively the collapsed reservoir may be configured as a flexible pouch portion provided on a rigid support portion (e.g. having a blister-like form), where at least a major portion of the walls defining the interior chamber of the reservoir when the reservoir is in an extended or expanded state is made of a flexible material.

In some embodiments the end of the needle near to the collapsible reservoir may be directly or indirectly mounted to the reservoir so that prior to actuation the lumen of the needle is in fluid communication with the interior chamber of the collapsible reservoir (and thus the medicinal liquid contained therein). For such embodiments it may be desirable to block to the distant end of the needle (e.g. by the septum), which in turn may potentially allow for the use of medicinal liquid formulations without preservatives. In other embodiments fluid communication between the collapsible reservoir and the needle may be first established during the actuation of the device, for example by the near end of the needle puncturing the collapsible reservoir during actuation. Such embodiments are also advantageous in that they also potentially allow for the use of medicinal liquid formulations without preservatives.

Favorably the device may further comprise a housing, wherein prior to injection, the dose assembly is disposed in the housing such that the collapsible reservoir and the needle are located in the interior of the housing. More favorably, the housing may be non-extensible and/or non-compressible along or in parallel to said longitudinal axis. It has be found that the provision of such a housing may be advantageous in that it underlines the ergonomic use of the device for example by providing stability along axis of injection and thus facilitating the application of force by the user which can be described as a squeezing action.

Desirably the at least one actuator element may be disposed onto the housing and has an outward-facing surface positioned laterally and to the exterior of the housing onto which the user may apply said force.

The housing may favorably comprise a septum, and wherein prior to injection, the septum blocks the lumen of the needle at the end of the needle distant to the collapsible reservoir.

The at least one actuator element and dose assembly may be favorably configured and arranged such that in response to an actuation force, the needle is displaced towards the septum, so that the needle is urged to pierce the septum, opening the lumen of the needle for fluid passage and the collapsible reservoir is urged to a collapsed state thereby expelling the medicinal liquid contained in the reservoir through the lumen of the needle.

To facilitate construction as well as compression of the reservoir to aid in expelling medicinal liquid from the reservoir, the collapsible reservoir may in some embodiments include in part a rigid support or in other embodiments the collapsible reservoir be arranged on a rigid support e.g. provided as part of the dose assembly. Depending on the particular arrangement of the device, the rigid support may favorably, generally extend along a plane perpendicular to the longitudinal axis or a plane parallel to or containing the longitudinal axis and wherein the at least one actuator element and dose assembly are configured and arranged such that as the collapsible reservoir is urged to a collapsed state, the collapsible reservoir is compressed in a direction towards the support and substantially perpendicular to the plane defined by support.

In some embodiments, the device may be configured and arranged such that the needle is retracted back into the device or housing, as the case may be, in response to a continued force being applied by the user onto the at least once actuator element after dispensation of the medicinal liquid. For example the at least one actuator element and the dose assembly may be desirably configured and arranged, such that the needle is to be displaced inwardly in response to a further force being applied by the user onto the at least one actuator element after dispensation of the medicinal liquid from the reservoir, so that the needle is retracted back through or into the septum thereby encasing the needle within the housing.

In other embodiments, the device may be configured and arranged such that the needle is retracted back into the device or housing, as the case may be, upon release of the at least one actuator element. For example, the at least one actuator element and the dose assembly may be favorably configured and arranged, such that the needle is to be displaced inwardly in response to a release of force by the user onto the at least one actuator element, so that the needle is retracted back through or into the septum thereby encasing the needle within the housing.

In yet other embodiments, the device may be configured and arranged such that the needle is automatically retracted back into the device or housing, as the case may be, just after the dispensation of the medicinal liquid from the reservoir is completed. For example, the at least one actuator element and the dose assembly may be desirably configured and arranged, such that the needle is to be displaced inwardly once dispensation of the medicinal liquid from the reservoir is completed, so that the needle is retracted back through or into the septum thereby encasing the needle within the housing.

Devices described herein may be favorably used for delivering one or more of the following: an analgesic, an anticoagulant, insulin, an insulin derivate, heparin, enoxaparin, a vaccine, a growth hormone, a peptide, a protein, an antibody, a carbohydrate, a polysaccharide, a nucleic acid, and a dual agonist, such as GLP-GCGR (glucagon-like peptide-glucagon receptor) and GLP-GiP (glucagon-like peptide-glucose-dependent insulinotropic polypeptide).

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Certain aspects will become more fully understood from the detailed description given hereinbelow and the accompanying drawings which are given by way of illustration only, and thus, are not limiting of the present invention, and wherein.

Corresponding parts are marked with the same reference symbols in all figures.

DETAILED DESCRIPTION

FIGS. 1A-D show a first exemplary embodiment of a device 1 for administering a medicinal liquid.

Figure 1:
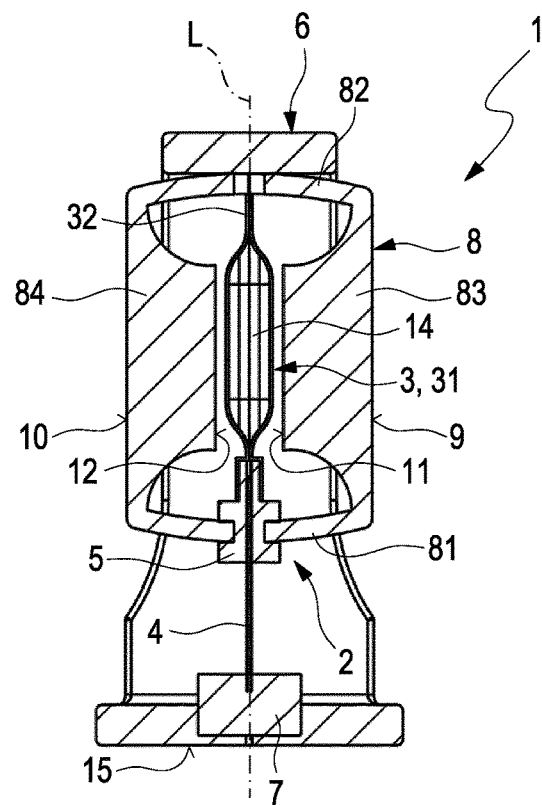
FIG. 1A represents a longitudinal cross-sectional view of a first exemplary embodiment according to the present invention, showing the device prior to injection and application of an actuation force (deployed position).
FIG. 1B represents a longitudinal cross-sectional view of a first exemplary embodiment, showing the device in an intermediate position during application of actuation force, wherein medicinal liquid is not yet dispensed.
FIG. 1C represents a longitudinal cross-sectional view of a first exemplary embodiment, showing the device upon completion of the application of the actuation force, wherein medicinal liquid is dispensed (dispensed position).
FIG. 1D represents a longitudinal cross-sectional view of a first exemplary embodiment, showing the device after the medicinal liquid has been dispensed and release of the actuation force, wherein the needle is retracted (retracted position).
Figure 1:
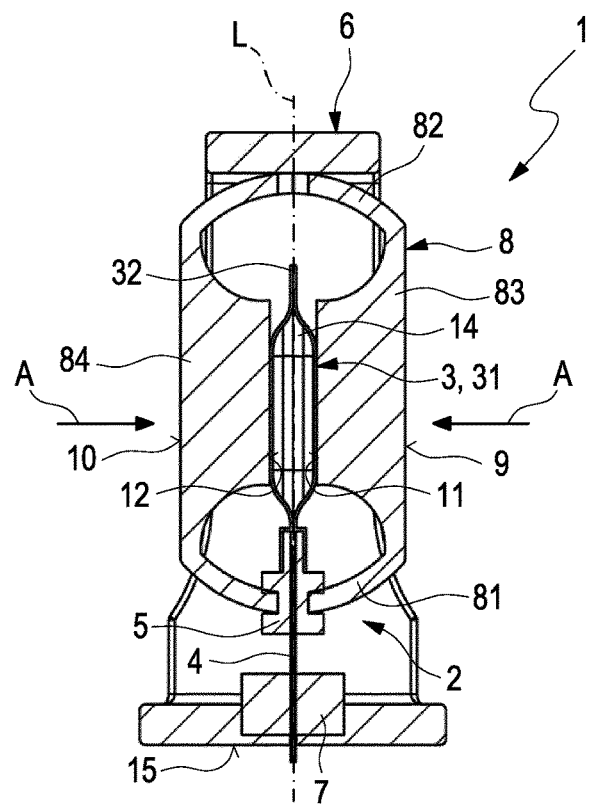
Figure 1:
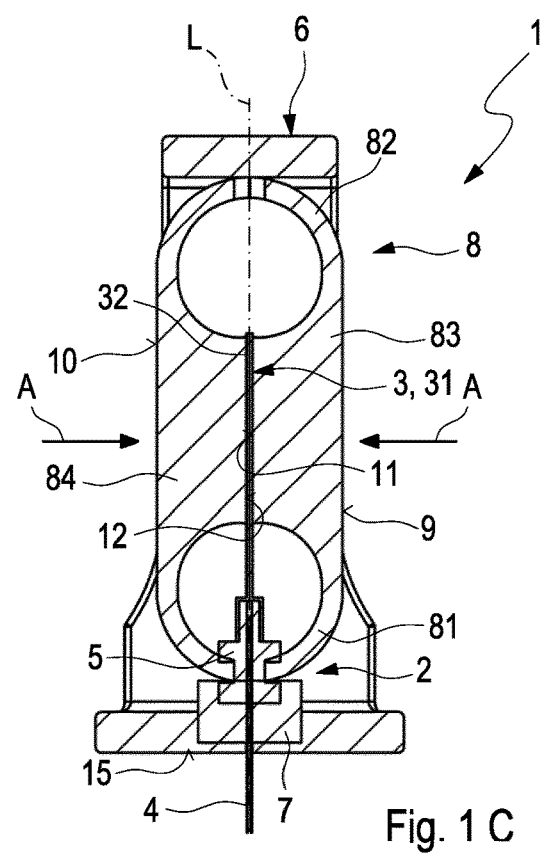
Figure 1:
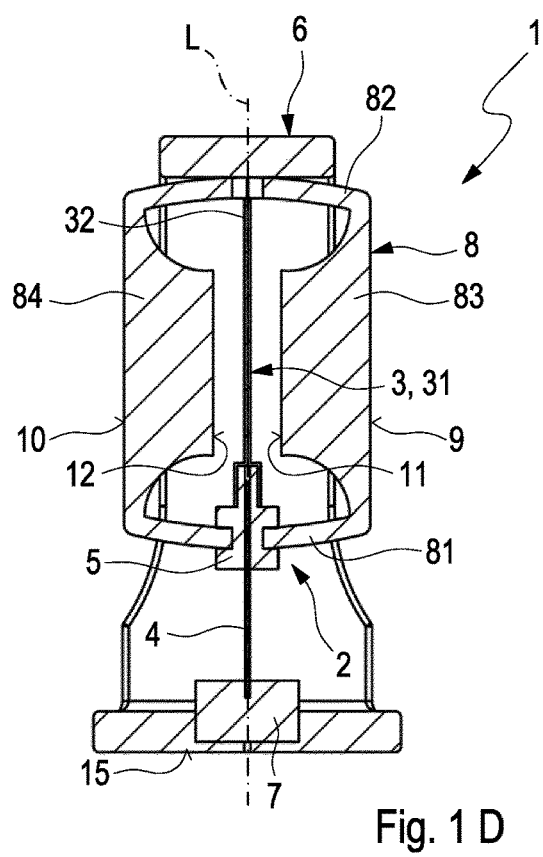

Referring to FIG. 1A, the first exemplary embodiment comprises a dose assembly 2 comprising a collapsible reservoir 3 and an injection needle 4, wherein at least a major portion of the needle 4 (in this particular exemplary embodiment the entire portion thereof) defines a longitudinal axis L. The walls of the collapsible reservoir 3 are made of a flexible material. The collapsible reservoir is favorably configured as a flexible ampoule 31 and is supported substantially along its circumference by an essentially planar, ring-formed, rigid support 32, the planar support generally aligned along/parallel to the longitudinal axis L. The injection needle 4 is hollow and thus has a lumen (not visible in the drawing). In the exemplary embodiment, a sleeve-like connector 5 is arranged on the distal end portion of the needle 4 near the reservoir 3 and the connector is coupled to a proximal portion of the reservoir so that, via the distal end of the needle, the lumen of the needle is in fluid communication with the reservoir in particular with the interior cavity of the reservoir. The first exemplary embodiment includes a housing 6. The housing 6 includes two opposing, lateral elongate openings or cut-outs. The housing comprises a septum 7, the septum being located near one end, i.e. the proximal end, of the housing. Prior to injection, the septum blocks the lumen of the needle at the second, proximal end of the needle. Also prior to injection, the needle 4 in its entirety as well as the collapsible reservoir 3 are located within the interior of the housing 4. The exemplary embodiment includes an actuator element 8 onto which the user may apply a force to actuate the device. In the first exemplary embodiment, the actuator element is generally configured as a substantially rectangular, open-ended box-like element. Two opposing end portions 81, 82 of the actuator element 8 generally perpendicular the longitudinal axis L are generally configured as outwardly bendable walls or arms, the proximal end portion 81 is centrally mounted to the connector 5 and the opposing distal end portion 82 of the actuator element 8 is centrally mounted to the housing near its distal end. The side portions 83, 84 of the actuator element 8 extend outwardly through the lateral openings in the housing 6. The side portions 83, 84 of the actuator element 8 include two surfaces 9, 10 positioned laterally and externally to the housing 6 and onto which the user may press in order to apply a force to actuate the device 1. In addition, the side portions 83, 84 of the actuator element 8 includes two inner surfaces 11, 12 that will engage and thus act on at least a portion of the dose assembly (in particular onto the collapsible reservoir 3, more particular onto the ampoule 31), during operation of the device. Referring to FIGS. 1A and D, the reservoir 3 is located within an open interior space within the non-actuated and/or released actuator element 8. If desired, the housing 6 may include a viewing window which may be a transparent portion of the housing or an additional cut-out so that the reservoir 3 can be viewed from the outside of the housing. The collapsible reservoir 3 generally has a maximum volume in its fully extended state and a minimum volume in its collapsed state. Referring to FIG. 1A prior to injection the reservoir 3 contains the medicinal liquid 14 to be administered and thus the reservoir is in an extended state. In particular, FIG. 1A shows the exemplary embodiment in its state or position ready for use, which is referred herein as the "deployed position".

In use of the first exemplary embodiment, the outer surface of the proximal end of the housing—i.e. the resting surface 15 (marked in FIG. 1A)—is placed e.g. by the user onto the targeted injection site. (In the aforesaid and the following, the use of "proximal" and "distal" is made having regarded to the resting surface.) Referring to FIG. 1B, the user then presses onto outer lateral surfaces 9, 10 of the actuator element 8, thus applying an inward actuation force from both sides (symbolized by "A→" in the drawing). In this exemplary embodiment, the applied actuation force is essentially completely along an axis perpendicular to the longitudinal axis L. As can be seen in FIG. 1B, as the actuation force is applied, the proximal and distal end portions 81, 82 of the actuator element 8 bow outwardly so that actuator element elongates along the longitudinal axis L within the housing (said housing being non-extensible and non-compressible along or in parallel to the longitudinal axis L), pushing the connector 5 towards the resting surface and thus displacing the needle along said longitudinal axis L towards the resting surface. In particular, referring to FIG. 1B, the needle is displaced towards the septum and urged to pierce the septum, so that the lumen of the needle is open for fluid passage from the reservoir to the targeted injection site. As can be appreciated FIGS. 1B and C, as the actuation force is continued to be applied, the needle is further displaced so that it extends outwardly beyond the resting surface 15 of housing. In addition, as can be seen in FIGS. 1B and C, as the actuation force is continued to be applied, the inner lateral surfaces 11, 12 of the actuator element come into contact with the outer lateral surfaces of a portion of the collapsible reservoir 3 (in particular with the outer surfaces of the ampoule 31) (see FIG. 1B) and the outer walls of collapsible reservoir are pressed or squeezed together so the reservoir is urged to a collapsed state (see FIG. 1C) thereby expelling the medicinal liquid 14 contained in the reservoir through the lumen of the needle 4. FIG. 1C shows the exemplary device 1 in its dispensed position, where the application of the actuation force is completed and the medicinal liquid 14 has been dispensed. FIG. 1D shows the exemplary device 1 in its retracted position, wherein upon release of the actuation force, in particular when the user discontinues to press onto outer lateral surfaces 9, 10 of the actuator element 8, the actuator element returns to its original form, thus pulling the connector 5 together with the needle 4 back inwardly away from the resting surface 15 and so that the needle is retracted back into (or through) the septum 7 thereby encasing the needle once again within the housing 6.

FIGS. 2A-D show a second exemplary embodiment of a device 1 for administering a medicinal liquid.

Figure 2:
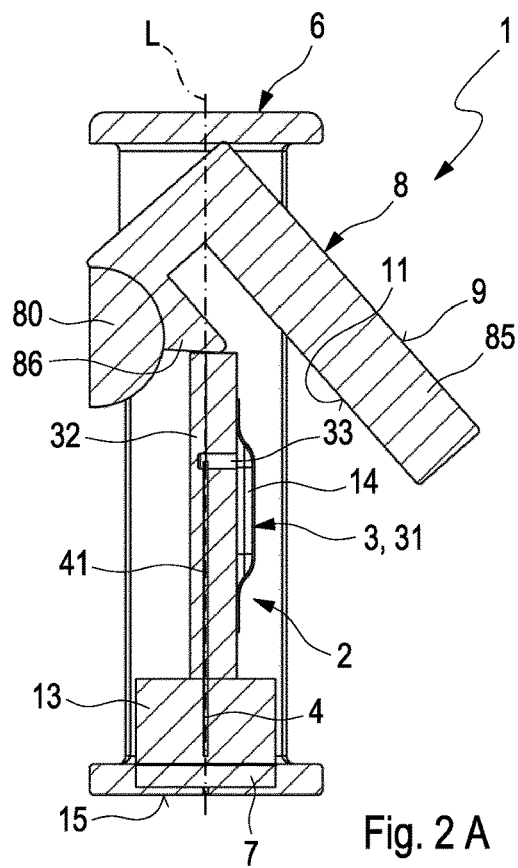
FIG. 2A represents a longitudinal cross-sectional view of a second exemplary embodiment according to the present invention, showing the device prior to injection and application of an actuation force (deployed position).
FIG. 2B represents a longitudinal cross-sectional view of a second exemplary embodiment, showing the device in an intermediate position during application of actuation force, wherein medicinal liquid is not yet dispensed.
FIG. 2C represents a longitudinal cross-sectional view of a second exemplary embodiment, showing the device just upon the completion of the application of the actuation force and the dispense of the medicinal liquid (dispensed position)
FIG. 2D represents a longitudinal cross-sectional view of a second exemplary embodiment, showing the device after the medicinal liquid has been dispensed, wherein the needle is retracted (retracted position).
Figure 2:
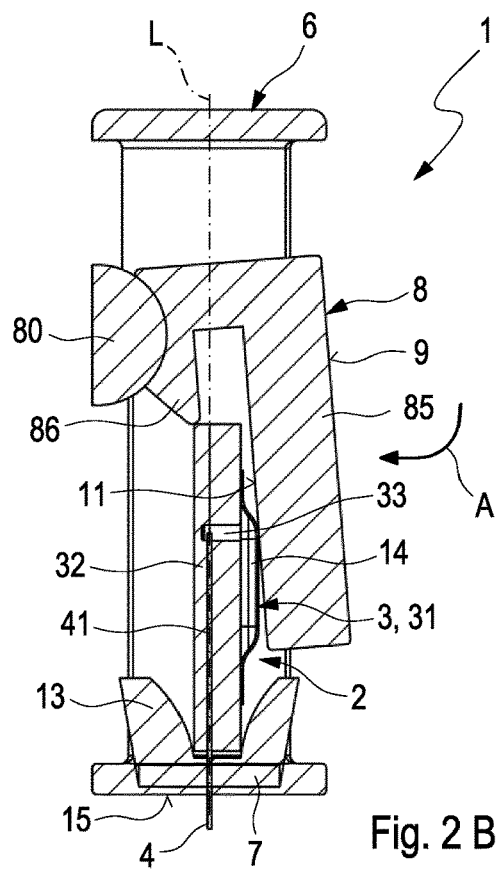
Figure 2:
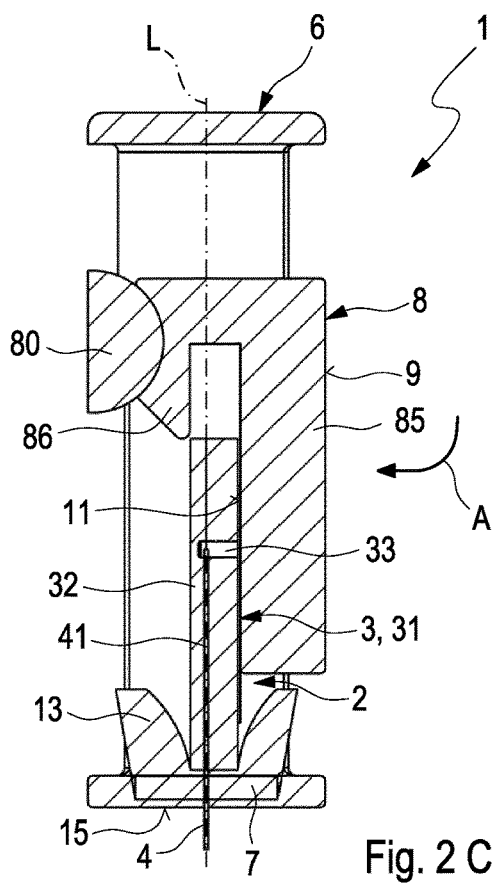
Figure 2:
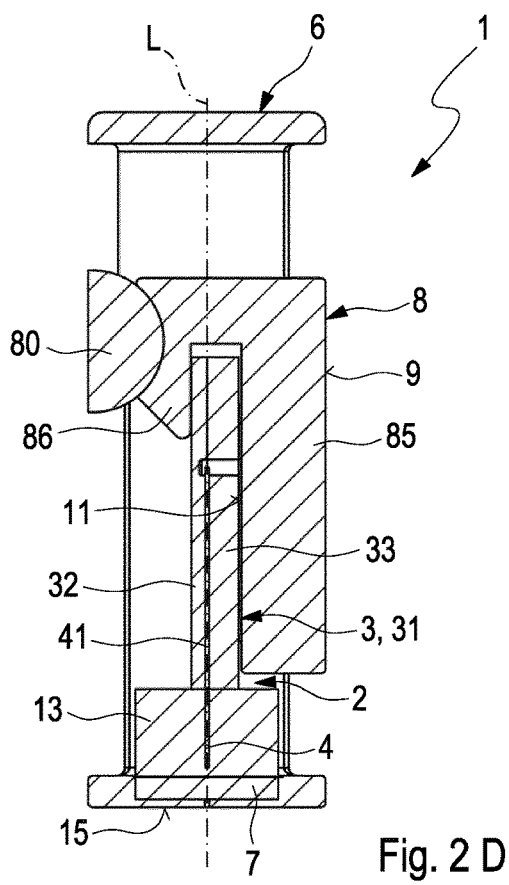

Referring to FIG. 2A, the second exemplary embodiment comprises a dose assembly 2 comprising a collapsible reservoir 3 and an injection needle 4, wherein at least a major portion of the needle (in this particular exemplary embodiment the entire portion thereof) defines a longitudinal axis L. A flexible pouch 31 is favorably provided on an essentially planar, rigid support 32, the planar support generally aligned along the longitudinal axis L, such that the flexible pouch together with the portion of the rigid support opposite the flexible pouch define the collapsible reservoir. The collapsible reservoir has an outlet (not visible in drawing) facing a passageway 33 in the support. Accordingly the walls of the collapsible reservoir are favorably made in part of a flexible material and in part of a rigid material, more favorably at least a major portion the walls of the collapsible reservoir are made of a flexible material. Advantageously the rigid support ensures stability of the pouch in the required position, while the flexibility of the pouch allows the drug to be squeezed out of the pouch for delivery through passageway 33. The injection needle 4 is hollow and thus has a lumen 41. In the exemplary embodiment, a distal portion of the needle 4 is mounted to and positioned within the planar support 32, wherein the distal end of the needle is located in the passageway 33 of the support, so that the lumen 41 of the needle is in fluid communication with the reservoir (in particular with the interior cavity of the reservoir, more particular with the interior of the collapsible pouch 31). The exemplary embodiment includes a housing 6, the housing being non-extensible and non-compressible along or in parallel to the longitudinal axis L. The housing 6 comprises a septum 7, the septum being located at the proximal end of the housing. Prior to injection, the septum 7 blocks the lumen 41 of the needle 4 at the second, proximal end of the needle. Also prior to injection, the needle 4 in its entirety as well as the collapsible reservoir 3 are located within the interior of the housing. Referring to FIG. 2A, the collapsible reservoir 3 is supported within the housing 6 through a ring 13 e.g. made of material having a shape-memory effect, such as a shape-memory polymer (or alternatively through a spring) provided around a proximal end portion of the needle 4, between the proximal end of the planar support 32 and the distal end of the septum 7. The exemplary embodiment includes an actuator element 8 onto which the user may apply a force to actuate the device 1. In this second exemplary embodiment, the actuator element 8 generally arranged and configured as lever-like element. A distal portion of the actuator element 8 is arranged on a pivot mount 80 provided on a portion of a side wall of the housing at a height between the distal end of the planar support 32 and the distal end of the housing. The actuator element has a generally inverted "J" form. A long arm 85 of the actuator element extends from the interior housing and externally through an elongate lateral opening in the housing opposite to the mount 80. An end portion of the long arm 85 extending to the outside the housing 6 provides an outwardly facing lateral surface 9 onto which the user may press in order to apply a force to actuate the device 1. A short arm 86 of the actuator element 8 extends from the mount within the housing, wherein an end portion of the short arm engages a distal end portion of the dose assembly 2, in particular the distal end of the planar support 32. Referring to FIG. 2A showing the exemplary embodiment in its deployed position ready for use, the reservoir contains the medicinal liquid 14 to be administered and thus the reservoir is in an extended state.

In use of the second exemplary device 1, the resting surface 15 at the proximal end of the housing 6 is placed by the user onto the targeted injection site. Referring to FIG. 2B, the user then presses onto outwardly facing lateral surface 9 of the long arm 85 the actuator element 9, said applied actuation force (see A→) having a component along an axis perpendicular to the longitudinal axis L. As can be seen in FIG. 2B, as the actuation force is applied, the actuator element pivots at the mount 80 and the inner short arm 86 acts on the dose assembly, in particular pushing the planar support 32 towards the resting surface, compressing the ring 13 and thus displacing the needle 4 along said longitudinal axis L. In particular, the needle is displaced towards the septum and urged to pierce through the septum, so that the lumen of the needle is open for fluid passage from the reservoir and further the needle is displaced so that it extends outwardly beyond the resting surface 15 of the housing. In addition, as can be appreciated from FIGS. 1B and C, as the actuation force is continued to be applied, a portion of the inner lateral surface 11 of the long arm 85 of the actuator element 8 comes into contact with a portion of the collapsible reservoir 3 (in particular with a portion of the outer lateral wall of the collapsible pouch 31) (see FIG. 2B) and presses onto the collapsible reservoir, so that the reservoir is urged to a collapsed state (see FIG. 2C) thereby expelling the medicinal liquid contained in the reservoir through the lumen 41 of the needle 4. FIG. 2C shows the exemplary embodiment in its dispensed position, where the application of the actuation force is just completed and the medicinal liquid has been dispensed. FIG. 2D shows the exemplary device 1 in its retracted position, and comparing FIGS. 2C and D, it can be seen that just after the completion of the actuation force application and dispensation of the medicinal liquid, the proximal end of the inner short arm 83 of the actuator element 8 disengages from the distal end of the planar support 32 and the ring 13 returns to its original form thus pushing the planar support 32 together with the needle 4 back inwardly away from the resting surface 15 and so that the needle is retracted back into (or through) the septum 7 thereby encasing the needle within the housing 6.

FIGS. 3A-E show a third exemplary embodiment of a device 1 for administering a medicinal liquid.

Figure 3A:
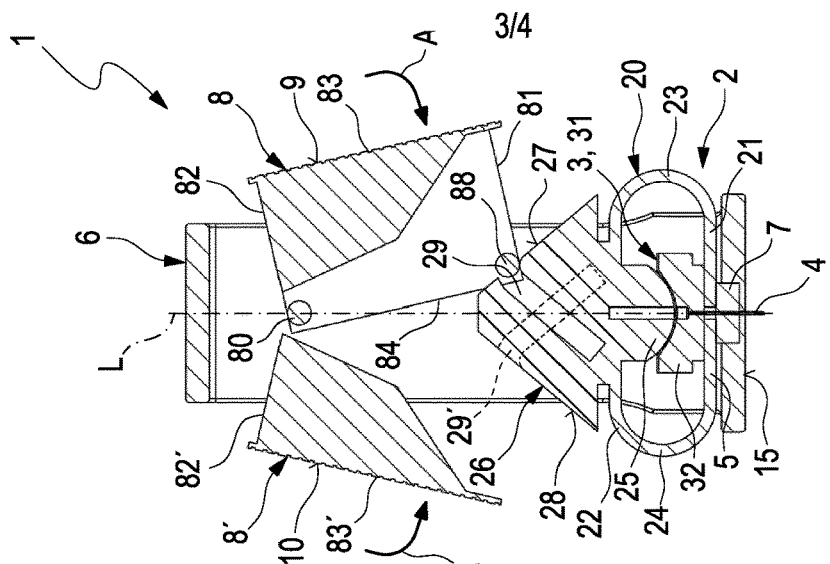
FIG. 3A represents a longitudinal cross-sectional view of a third exemplary embodiment according to the present invention, showing the device prior to injection and application of an actuation force (deployed position).

Referring to FIG. 3A, the third exemplary embodiment comprises a dose assembly 2 comprising a collapsible reservoir 3 and an injection needle 4, wherein at least a major portion of the needle (in this particular exemplary embodiment the entire portion thereof) defines a longitudinal axis L. The injection needle 4 is hollow and thus has a lumen (not visible in the drawings). In the exemplary embodiment, a distal end of the needle 4 is mounted to the collapsible reservoir via a connector 5 so that the lumen of the needle is in fluid communication with the reservoir in particular with the interior cavity of the reservoir. The walls of the collapsible reservoir are made of a flexible material. The collapsible reservoir is favorably configured as a flexible ampoule 31 and is supported on a rigid support 32, the support being generally aligned perpendicular to the longitudinal axis L and having a depression in which a part of the reservoir is located. In addition, the dose assembly further comprises a housing 20, referred to in the following as a "carriage", where the collapsible reservoir 3 is located in the interior cavity of the carriage, the support 32 arranged on a portion of the interior surface of the proximal end portion 21 of the carriage. The needle 4 extends through proximal walls of both the support 32 and the carriage 20, so that a major portion of needle together with its proximal end extends beyond the outer proximal surfaces of the support and carriage. The two opposing lateral portions 23, 24 of the carriage are configured as outwardly bendable walls. The inner surface of the distal end portion 22 of the carriage is provided with an extension 25 extending into the interior cavity of the carriage. The proximal end of the extension has a convex surface conforming to the concave surface of the depression of the support. Prior to injection, the outermost proximal surface of the extension is nearly in contact or is just in contact with the outermost distal surface of the collapsible reservoir. The outer part (i.e. outer relative to the interior cavity of the carriage) of the distal end portion 22 of the carriage 20 is provided with a structure 26 (described in more detail below) that together and in cooperation with two actuator elements 8, 8' (described below) provide a type of travel and suspension system for movement of the carriage, said movement being along or parallel to the longitudinal axis L.

The exemplary embodiment includes a housing 6. The housing is generally non-extensible and non-compressible along or in parallel to the longitudinal axis L. The housing comprises a septum 7, the septum being located at the proximal end of the housing. The housing includes two opposing, lateral elongate openings or cut-outs. Referring to FIG. 3A prior to injection, the carriage is positioned in the housing spaced apart from the distal surface of the septum so that the septum blocks the lumen of the needle at the proximal end of the needle. Also referring to FIG. 3A, prior to injection, the needle in its entirety as well as the collapsible reservoir are located within the interior of the housing while the carriage is in part located within the interior of the housing and in part to the exterior of the housing, in particular the lateral wall portions 23, 24 of the carriage extend outwardly through the lateral openings in the housing.

The exemplary embodiment includes two actuator elements 8, 8' onto which the user may apply a force to actuate the device 1. Referring to FIG. 3A, it can be appreciated that the actuator elements 8, 8' extend outwardly through the lateral openings in the housing 6 so that outward-facing side portion 83, 83' of each actuator element is positioned to the exterior of the housing. Each of these side portions includes a surface 9, 10 positioned laterally and thus externally to the housing. The two surfaces 9, 10 are positioned generally opposite to one another, and the user may press or squeeze onto the surfaces which in order to apply a force to actuate the device 1. The distal end portion 82, 82' of each actuator element 8, 8' is provided with a mount pin 80, 80' (80' not visible in the drawings) in particular at a position near their respective inward-facing side portion 84, 84' (84' not visible). Each actuator element is mounted to the housing, in particular at opposing positions on the interior surface of the housing, near the distal end of the housing, such that each actuator element is able to pivot or rotate inwardly and towards the other actuator elements about the mount pin 80, 80'. The proximal end portion 81, 81' (81' not visible) of each actuator element 8, 8', is provided with an engagement pin 88, 88' (88' not visible) in particular at a position near their inward-facing side portion 84, 84' (84' not visible). Referring to FIG. 3A, the engagement pins 88, 88' of the actuator elements 8, 8' are in engagement with and thus will act on at least a portion of the dose assembly 2, in particular onto the structure 26 of the carriage 20 of the dose assembly, during operation of the device 1. In particular, the structure 26 of the carriage has a general, triangular form with two outer lateral surfaces 27, 28 extending distally to a central apex or plateau portion. In addition the structure 26 is provided with two dead-end, non-intersecting internal guide-passages 29, 29' (the passage 29' is shown with dashed lines in FIG. 3A to E), the openings of the guide-passages located on the two outer lateral surfaces near, but on opposing sides, of the central apex or plateau portion of the structure. Each passage 29, 29' extends from its opening at one outer lateral surface 27, 28 proximally and generally parallel to the other outer lateral surface 28, 27. The portions of outer lateral surfaces 27, 28 up to the guide-passage openings and the interior surfaces of guide-passages 29, 29' of the carriage structure 26 provide surfaces for engagement and travel of the engagement pins. Referring to the FIGS. 3A-E, it will be appreciated that the engagement and travel surface for each engagement pin generally has an approximate inverted "V" form. Referring to FIG. 3A showing the exemplary embodiment in its deployed position ready for use, the reservoir contains the medicinal liquid 14 to be administered and thus the reservoir is in an extended state.

Figure 3B:
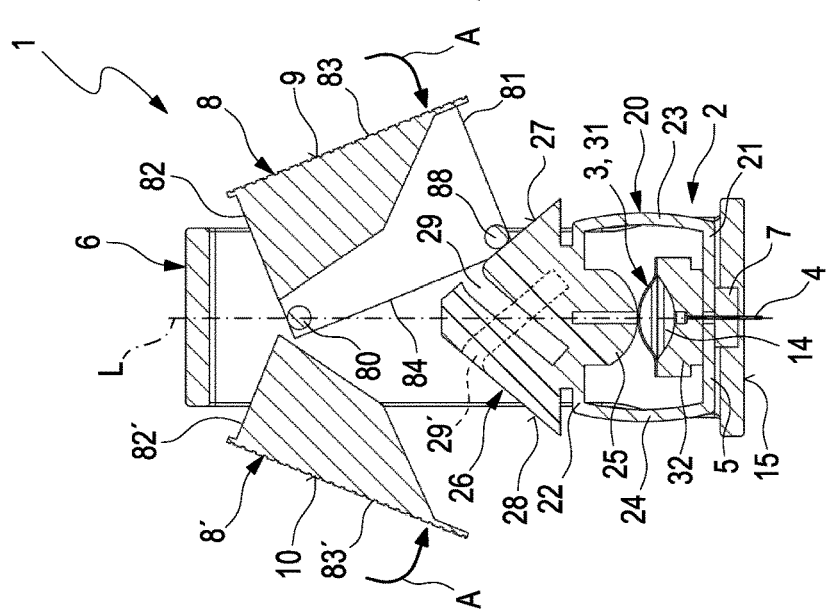
FIG. 3B represents a longitudinal cross-sectional view of a third exemplary embodiment, showing the device in an intermediate position during application of actuation force, wherein medicinal liquid is not yet dispensed.
Figure 3C:
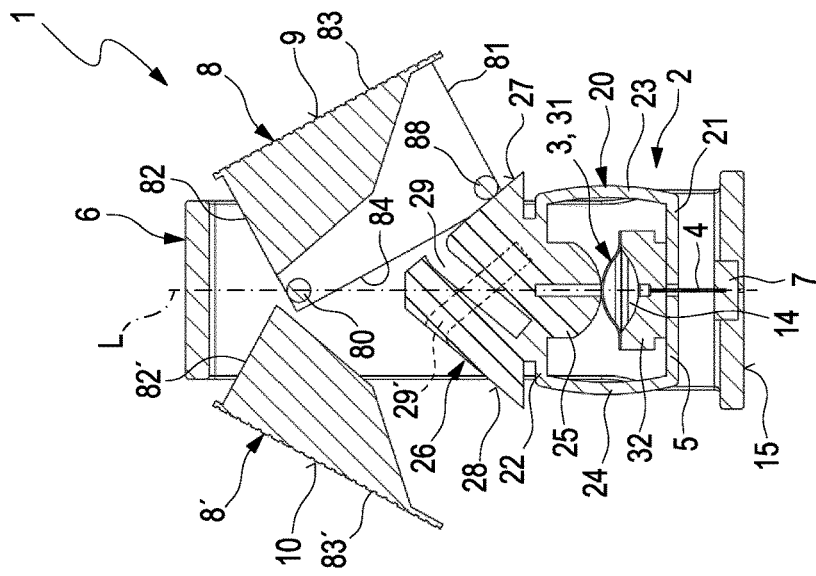
FIG. 3C represents a longitudinal cross-sectional view of a third exemplary embodiment, showing the device wherein medicinal liquid is dispensed (dispensed position).
Figure 3:
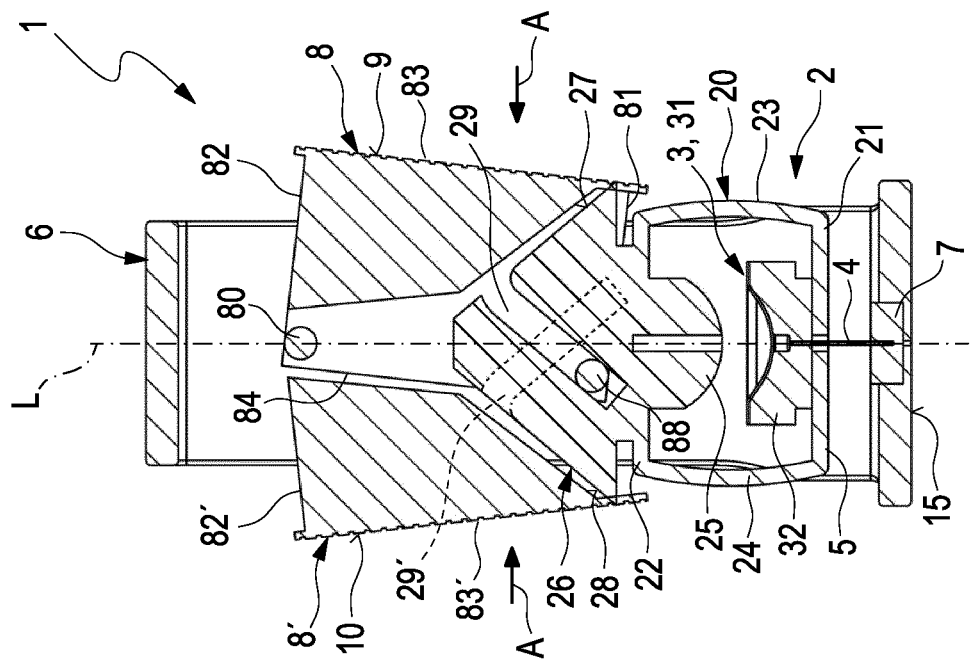
FIG. 3D represents a longitudinal cross-sectional view of a third exemplary embodiment, showing the device after the medicinal liquid has been dispensed and further application of actuation force, wherein the needle is not yet retracted.
FIG. 3E represents a longitudinal cross-sectional view of a third exemplary embodiment, showing the device after the medicinal liquid has been dispensed and completion of the application of the actuation force, wherein the needle is retracted (retracted position).
Figure 3:
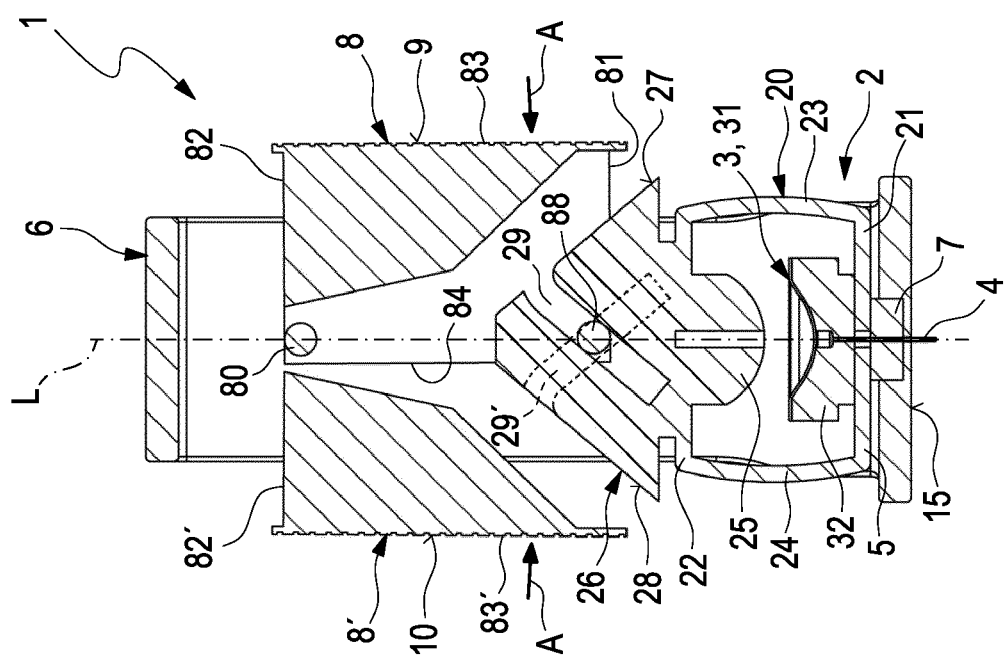

In use of the third exemplary embodiment, the resting surface 15 at the proximal end of the housing 6 is placed by the user onto the targeted injection site. Referring to FIG. 3B, the user then presses or squeezes onto outwardly facing lateral surfaces 9, 10 of the actuator element, said applied actuation force (see A→) having a component along an axis perpendicular to the longitudinal axis L. As can be seen in FIG. 3B, as the actuation force is applied, each the actuator element 8, 8' pivots inwardly and acts on the dose assembly 2, in particular each engagement pin 88, 88' travels distally along the respective outer lateral surface 27, 28 of the carriage structure 26 and thus pushing carriage 20 towards the resting surface and correspondingly displacing the needle 4 along said longitudinal axis L. In particular, the needle 4 is displaced towards the septum 7 and urged to pierce through the septum, so that the lumen of the needle is open for fluid passage from the collapsible reservoir 3 and further the needle is displaced so that it extends outwardly beyond the resting surface 15 of the housing 6. In addition, as can be appreciated from FIGS. 3B and C, as the actuation force is continued to be applied and each engagement pin 88, 88' travels distally along the respective outer lateral surface 27, 28 of the carriage structure 26 up to the openings of the respective passages 29, 29', the two opposing lateral portions 23, 24 of the carriage 20 bow outwardly and the extension 25 presses onto the collapsible reservoir 3 so the reservoir is urged to a collapsed state (see FIG. 3C) thereby expelling the medicinal liquid contained in the reservoir through the lumen of the needle 4. FIG. 3C shows the third exemplary device 1 in its dispensed position, wherein the medicinal liquid has been just dispensed. FIG. 3E shows the third exemplary device in its retracted position. Referring FIGS. 3D and E, it can be seen that after the completion of the dispensation of the medicinal liquid (see FIG. 3C), as the user continues to presses onto outwardly facing lateral surfaces 9, 10 of the actuator elements 8, 8', each the actuator element pivots further inwardly and each engagement pin 88, 88' of each actuator element travels proximally along the respective passages 29, 29' of the carriage structure 26, de-compressing the carriage 20 (i.e. allowing the lateral walls 23, 24 of the carriage to return to their original form) (see FIG. 3D) and subsequently pulling the carriage distally away from the resting surface 15, thus displacing the needle 4 inwardly along said longitudinal axis L, so that the needle is retracted back through or into the septum 7 thereby encasing the needle once again within the housing 6 (see FIG. 3E).

To facilitate the piercing of the septum and aid in ensuring that during the application of the actuation force that the needle first pierces the septum and the thereafter medicinal liquid is pressed through the lumen, desirably the septum is made of a material, in particular an elastomeric or rubber material, having a Shore A hardness as measured in according to DIN 53505 of 65 or less, more desirably of 60 or less, and most desirably 55 or less. To aid in prevent accidental piercing of the septum e.g. during storage and general handling, desirably the septum is made of a material having a Shore A hardness of 30 or more, more desirably 40 or more, most desirably 45 or more.

The term "medicinal liquid" as used herein means a liquid pharmaceutical formulation containing at least one pharmaceutically active compound, said at least one pharmaceutical active compound being either dissolved or suspended. As described below, the medicinal liquid can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these pharmaceutically active compounds are also contemplated.

The devices and medicinal liquids described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary pharmaceutically active compounds for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in devices described herein. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

In devices described herein the collapsible reservoir may favorably contain a single dose of medicinal liquid to be administered. Single doses of medicinal liquid may typically have a volume of 1000 µl or less, in particular 750 µl or less, more particularly 500 µl or less, even more particularly 10 µl to 500 µl. The dose assembly or alternatively the device as a whole made be favorably designed to be disposable and/or small in size, the latter being advantageous in terms of storage and handling.

The reservoir may be configured to provide a suitable chamber for storage (e.g., short- or long-term storage) of one or more pharmaceutically active compounds. For example, in some instances, the reservoir may be designed to store a drug for at least one day (e.g., 1 to at least 30 days). In some instances, the reservoir may be designed to store a drug for about 1 month to about 2 years. Storage may occur at room temperature (e.g., about 20° C.), or refrigerated temperatures (e.g., from about −4° C. to about 4° C.). It has been advantageous found that the device and the reservoir can be favourable configured to allow for long-term storage while at the same time using a medicinal liquid that is free of preservatives.

Generally when the collapsible reservoir contains the medicinal liquid to be administered, the reservoir is in an extended or expanded state, and when the medicinal liquid has been dispensed, the collapsible reservoir is in a collapsed state. As discussed in the exemplary embodiments, at least a major portion of the walls (and in some embodiments essentially all the walls) of the collapsible reservoir is (are) favorably made of a flexible material. Moreover at least a major portion of the walls of the reservoir is favorably made of a material that is flexible, such that when the reservoir contains the medicinal liquid to be administered the at least major portion of the walls is in an extended or expanded state and when the reservoir is empty or the medicinal liquid has been dispensed the at least major portion of the walls is in a collapsed state. For example, the collapsible reservoir may be configured as a flexible pouch or ampoule. The collapsible, flexible walls of the collapsible reservoir may be made of a polymeric containing film having either a monolayer or a multi-layer (e.g. laminate) structure. The polymeric materials may be selected from the group consisting of polyester, polypropylene, cyclic-olefin polymer, cyclic olefin copolymer, polychlorotrifluoroethylene, ethylene vinyl alcohol copolymer and combinations thereof. Examples of suitable commercially available materials include ZEONEX™ COP 5000 monolayer; TEKNIFLEX™ CPTA (COC/LDPC/PCTFE laminate); TEKNI-PLEX™ PTA260 (PE/PCTFE laminate); TEKNI-PLEX™ PTA360 (PE/PCTFE laminate); TEKNI-PLEX™ PTA2200 (PE/PCTFE laminate); TEKNI-PLEX™ PTOA2200 (PE/EVOH/PCTFE laminate); HUHTAMAKI™ 602204276 (PET/Al/PP laminate); HUHTAMAKI™ 10224247983 (PET-AlOx/PET/PP laminate); SPAETER™ films made of a PET-SiOx film layer laminated with either a BAREX™ or TPE film layer.

Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

LIST OF REFERENCE NUMBERS 1 device
2 dose assembly
3 collapsible reservoir
31a collapsible pouch
32 support
33 passageway
4 injection needle
41 lumen
5 connector
6 housing
7 septum
8 actuator element
80 mount
81 proximal end portion of actuator element
82 distal end portion of actuator element
83, 84 lateral side portions of actuator element
85 long arm
86 short arm
87 extension
88 engagement pin
9, 10 outer lateral surfaces of actuator element
11, 12 inner lateral surfaces of actuator element
13 ring
14 medicinal liquid
15 resting surface
20 carriage
21 proximal end portion of the carriage
22 the distal end portion of the carriage
23, 24 two opposing lateral portions of the carriage 25 extension of the carriage
26 carriage structure
27, 28 outer travel surface of carriage structure
29 guide passage in carriage structure
L longitudinal axis L
A force

The invention claimed is:

1. A device for administering a medicinal liquid by injection, the device comprising:
 a dose assembly comprising
  a collapsible reservoir, wherein the collapsible reservoir is adapted to hold the medicinal liquid to be administered; and
  an injection needle having a lumen, wherein at least a major part of the needle defines a longitudinal axis, wherein prior to injection the needle is located in an interior of the device and wherein a first end of the needle near the collapsible reservoir is directly or indirectly mounted to the reservoir so that prior to an actuation of the device by a user the lumen of the needle is in fluid communication with an interior chamber of the collapsible reservoir;
 at least one actuator element onto which a user may apply a force to actuate the device, the force having a perpendicular force component along an axis perpendicular to the longitudinal axis; and
 a housing comprising a septum, wherein prior to injection, the dose assembly is disposed in the housing such that the collapsible reservoir and the needle are located in an interior of the housing and the septum blocks the lumen of the needle at a second end of the needle distal to the collapsible reservoir;
 wherein the at least one actuator element is configured and arranged to act on at least a portion of the dose assembly and the collapsible reservoir along the axis perpendicular to the longitudinal axis through a first movement and a second movement subsequent and continuous to the first movement without an intervening movement, along the axis perpendicular to the longitudinal axis, wherein the at least one actuator element and the dose assembly are configured:
  i) such that the first movement of the at least one actuator element causes a displacement of the needle along the longitudinal axis and/or along an axis parallel to the longitudinal axis so that a portion of the needle moves from the interior of the housing to an exterior of the housing to allow for dispensation of the medicinal liquid, and
  ii) such that the second movement of the at least one actuator element causes a collapsing of the collapsible reservoir to a collapsed state, thereby expelling the medicinal liquid contained in the reservoir through the lumen of the needle; and
 wherein the septum is made of an elastomeric or rubber material having a Shore A hardness of 30-65.

2. The device according to claim 1, wherein the at least one actuator element and the dose assembly are configured, such that after the dispensation of the medicinal liquid and/or release of the at least one actuator element by the user, the portion of the needle moves from the exterior of the housing to the interior of the housing.

3. The device according to claim 1, wherein the collapsible reservoir contains a single dose of medicinal liquid to be administered.

4. The device according to claim 3, wherein the single dose of medicinal liquid to be administered has a volume of 1000 µl or less.

5. The device according to claim 1, wherein at least a major portion of walls of the collapsible reservoir is made of a flexible material.

6. The device according to claim 5, wherein when the collapsible reservoir contains the medicinal liquid to be administered, the at least major portion of the walls of the reservoir is in an extended or expanded state, and when the medicinal liquid has been dispensed, the at least major portion of the walls of the reservoir is in a collapsed state.

7. The device according to claim 1, wherein the collapsible reservoir is configured as a flexible pouch or ampoule.

8. The device according to claim 1, wherein the housing is non-extensible and/or non-compressible along or in parallel to the longitudinal axis.

9. The device according to claim 1, wherein the at least one actuator element is disposed onto the housing and has an outward-facing surface positioned laterally and to the exterior of the housing onto which the user may apply the force.

10. The device according to claim 1, wherein the at least one actuator element and the dose assembly are configured such that in response to the force: the needle is displaced towards the septum so that the needle is urged to pierce the septum, opening the lumen of the needle for fluid passage, and the collapsible reservoir is urged to a collapsed state thereby expelling the medicinal liquid contained in the reservoir through the lumen of the needle.

11. The device according to claim 10, wherein the at least one actuator element and the dose assembly are configured such that the needle is displaced inwardly in response to a further force being applied by the user onto the at least one actuator element after the dispensation of the medicinal liquid from the reservoir, wherein the needle is configured to be retracted back through or into the septum and to be encased within the housing in response to the further force being applied by the user.

12. The device according to claim 10, wherein the at least one actuator element and the dose assembly are configured such that the needle is displaced inwardly in response to a release of the force by the user onto the at least one actuator element, wherein the needle is configured to be retracted back through or into the septum and to be encased within the housing in response to the release of the force by the user.

13. The device according to claim 10, wherein the at least one actuator element and the dose assembly are configured and arranged such that the needle is displaced inwardly once the dispensation of the medicinal liquid from the reservoir is completed, wherein the needle is configured to be retracted back through or into the septum and to be encased within the housing once the dispensation of the medicinal liquid from the reservoir is completed.

14. The device according to claim 1, wherein the collapsible reservoir is arranged on or includes a rigid support.

15. The device according to claim 14, wherein the rigid support generally extends along a plane perpendicular to the longitudinal axis or a plane parallel to or containing the longitudinal axis, wherein the at least one actuator element and dose assembly are configured such that as the collapsible reservoir is urged to a collapsed state, the collapsible reservoir is compressed in a direction towards the support and substantially perpendicular to the plane defined by the support.

16. The device according to claim 1, wherein the at least one actuator element comprises one or more lateral surfaces on which the force is applied by the user.

17. The device according to claim 16, wherein the one or more lateral surfaces comprises a plurality of lateral surfaces, and the at least one actuator element comprises first and second portions configured to move toward one another to urge the collapsible reservoir to a collapsed state to initiate the dispensation of the medicinal liquid in response to the force applied by the user on the one or more lateral surfaces.

18. The device according to claim 16, wherein the at least one actuator element is configured to pivot relative to the housing to urge the collapsible reservoir to a collapsed state to initiate the dispensation of the medicinal liquid in response to the force applied by the user on the one or more lateral surfaces.

19. The device according to claim 18, wherein the at least one actuator element comprises a first side portion and a second side portion, wherein the first side portion comprises a first lateral surface of the one or more lateral surfaces, and the second side portion comprises a second lateral surface of the one or more lateral surfaces, and wherein the first side portion and the second side portion are configured to pivot relative to the housing to urge the collapsible reservoir to a collapsed state to initiate the dispensation of the medicinal liquid in response to the force applied by the user.

20. A device for administering a medicinal liquid by injection, the device comprising:
   a dose assembly comprising
      a collapsible reservoir, wherein the collapsible reservoir is adapted to hold the medicinal liquid to be administered; and
      an injection needle having a lumen, wherein at least a major part of the needle defines a longitudinal axis, wherein prior to injection the needle is located in an interior of the device and wherein a first end of the needle near the collapsible reservoir is directly or indirectly mounted to the reservoir so that prior to actuation the lumen of the needle is in fluid communication with an interior chamber of the collapsible reservoir;
   at least one actuator element onto which a user may apply a force to actuate the device, the force having a component along an axis perpendicular to the longitudinal axis; and
   a housing comprising a septum, wherein prior to injection, the dose assembly is disposed in the housing such that the collapsible reservoir and the needle are located in an interior of the housing and the septum blocks the lumen of the needle at a second end of the needle distal to the collapsible reservoir;
   wherein the at least one actuator element is configured and arranged to act on at least a portion of the dose assembly and wherein the at least one actuator element and the dose assembly are configured such that the force causes a first displacement of the at least one actuator element along the axis perpendicular to the longitudinal axis and a second displacement of the at least one actuator element along the axis perpendicular to the longitudinal axis, wherein the second displacement is subsequent and continuous to the first displacement without an intervening displacement, along the axis perpendicular to the longitudinal axis, wherein the first displacement of the actuator element causes a displacement of the needle along the longitudinal axis and/or along an axis parallel to the longitudinal axis so that a portion of the needle moves from the interior of the housing to an exterior of the housing to allow for dispensation of the medicinal liquid; and
   wherein the septum is made of an elastomeric or rubber material having a Shore A hardness of 30-65,
   wherein the at least one actuator element and dose assembly are configured such that in response to the force and the first displacement of the actuator element:
      the needle is displaced towards the septum so that the needle is urged to pierce the septum, opening the lumen of the needle for fluid passage,
      the collapsible reservoir is urged to a collapsed state thereby expelling the medicinal liquid contained in the reservoir through the lumen of the needle, and
   wherein the at least one actuator element and dose assembly are configured such that in response to a further force being applied by the user onto the at least one actuator element after the dispensation of the medicinal liquid from the reservoir, the further force causes the second displacement of the at least one actuator element along the axis perpendicular to the longitudinal axis, wherein the second displacement of the at least one actuator element causes the needle to be retracted back through or into the septum and to be encased within the housing.

* * * * *